United States Patent [19]

Pretzer et al.

[11] 4,239,924

[45] * Dec. 16, 1980

[54] ETHANOL FROM METHANOL

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[*] Notice: The portion of the term of this patent subsequent to Jan. 9, 1996, has been disclaimed.

[21] Appl. No.: 42,426

[22] Filed: May 25, 1979

Related U.S. Application Data

[63] Continuation-in-part of Ser. No. 930,339, Aug. 2, 1978, abandoned, which is a continuation-in-part of Ser. No. 876,109, Feb. 8, 1978, abandoned.

[51] Int. Cl.³ .............................................. C07C 27/00
[52] U.S. Cl. .................................. 568/902; 560/265; 568/671; 568/487
[58] Field of Search .......................................... 568/902

[56] References Cited

U.S. PATENT DOCUMENTS

| 3,248,432 | 4/1966 | Riley et al. | 568/902 |
| 3,285,948 | 11/1966 | Butter | 568/902 |
| 3,448,157 | 6/1969 | Slaugh et al. | 568/909 |
| 3,631,111 | 12/1971 | Tucci | 568/909 |
| 4,133,966 | 1/1979 | Pretzer et al. | 568/902 |

OTHER PUBLICATIONS

Wender et al, "Science", vol. 113 (1951), pp. 206–207.

Primary Examiner—Joseph E. Evans

[57] ABSTRACT

A process for selectively producing ethanol which comprises introducing into a reaction zone (1) methanol, (2) hydrogen, (3) carbon monoxide, (4) a cobalt tricarbonyl complex, (5) an iodine compound and (6) a ruthenium compound and then subjecting the contents of said reaction zone to an elevated temperature and an elevated pressure for a time sufficient to convert methanol to ethanol.

25 Claims, No Drawings

ETHANOL FROM METHANOL

This application is a continuation-in-part application of our U.S. patent application Ser. No. 930,339 filed Aug. 2, 1978 for A PROCESS FOR HOMOLOGATION OF METHANOL TO ETHANOL WITH HIGH SELECTIVITY USING A COBALT TRICARBONYL COMPLEX, AN IODINE PROMOTER AND A RUTHENIUM COMPOUND, and now abandoned, which application, in turn, is a continuation-in-part application of our U.S. patent application Ser. No. 876,109, filed Feb. 8, 1978 for A PROCESS FOR HOMOLOGATION OF METHANOL TO ETHANOL WITH HIGH SELECTIVITY USING A COBALT TRICARBONYL COMPLEX, AN IODINE PROMOTER AND A RUTHENIUM COMPOUND, and now abandoned.

BACKGROUND OF THE INVENTION

1. Field of the Invention

This invention is directed to a process for selectively producing ethanol which comprises introducing into a reaction zone (1) methanol, (2) hydrogen, (3) carbon monoxide, (4) a cobalt tricarbonyl complex, (5) an iodine compound and (6) a ruthenium compound and then subjecting the contents of said reaction zone to an elevated temperature and an elevated pressure for a time sufficient to convert methanol to ethanol.

2. Description of the Prior Art

Ethanol is a compound which has been used by man since time immemorial. Historically, ethanol has been produced for various purposes by the fermentation of common grains. However, within recent years synthetic processes have been developed to synthesize this alcohol for industrial use. Such synthetic processes permit the use of more economical starting materials than those used in the fermentation processes, and, additionally, permit production and reproduction of a more standardized product and more easily predictable yields of end product. Methanol can easily and economically be produced in great quantities from hydrogen and carbon monoxide or from almost anything containing carbon and hydrogen, for example, from methane to manure and from coal to crude oil residues. One such process for producing ethanol synthetically involves reacting methanol with carbon monoxide and hydrogen at elevated temperatures and pressures in the presence of a catalyst system.

The conversion of an alcohol, for example, methanol, to the primary alcohol containing one carbon atom more than the original alcohol, namely ethanol, is normally a tedious and time-consuming procedure involving a series of steps. Additionally, catalysts which possess acceptable activity generally tend to give a wide spectrum of products in addition to ethanol, for example, hydrocarbons and oxygenated hydrocarbons having a broad distribution of carbon atoms. This not only complicates the separation and recovery of desired products, but results in reduced yield of ethanol and erosion of reactants in the production of undesirable by-products.

The reaction of methanol with hydrogen and carbon monoxide to produce ethanol is appreciated and disclosed by the prior art. However, in general, most known processes produce an undesirably large mixture of alcohols, aldehydes, ketones and carboxylic acids in addition to the desired alcohol.

For example, U.S. Pat. No. 4,013,700, entitled "Catalytic Process for Polyhydric Alcohols and Derivatives," issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled "Process for the Production of Ethyl Alcohol," issued to Riley et al, on Apr. 26, 1966, which relates to a process for the production of ethyl alcohol by the interaction of methanol, carbon monoxide and hydrogen. In particular, these compounds are reacted at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled "Preparation of Organic Hydroxy-Containing Compounds by Reacting Alcohols With Carbon Monoxide and Hydrogen," issued to Greshaw on June 16, 1948, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts. The process, however, suffers from the disadvantage of poor product distribution.

U.S. Pat. No. 3,285,948, entitled "Halides of Ruthenium and Osmium In Conjunction With Cobalt and Iodine in the Production of Ethanol From Methanol", issued to Butter on Nov. 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, iodine or alkali metal iodines. A secondary promoter is also employed, i.e., ruthenium halide or osmium halide. High selectivity is described as better when the secondary promoter is used in combination with the primary promoter and other reactants.

Dutch Pat. No. 760.6138, entitled "Process for the Formation of Ethanol from Methanol and Synthesis Gas," issued to Shell International Research on June 8, 1976, relates to a process for producing alcohols which utilizes any soluble cobalt source which can generate a cobalt carbonyl or hydro carbonyl by reaction with synthesis gas. For example, sources of cobalt suitable for use are cobalt iodide or cobalt metal from which ions can be generated in situ. Organic salts of cobalt such as cobalt acetate, formate, or propionate are described as especially good sources; an iodide or bromide promoter is also utilized. In addition, the use of a tertiary phosphine is described as affording improved selectivity to the formation of alcohols.

SUMMARY OF THE INVENTION

The present invention relates to a process for selectively producing ethanol which comprises introducing into a reaction zone (1) methanol, (2) hydrogen, (3) carbon monoxide, (4) a cobalt tricarbonyl complex, (5)

an iodine compound and (6) a ruthenium compound and then subjecting the contents of said reaction zone to an elevated temperature and an elevated pressure for a time sufficient to convert methanol to ethanol.

From the above it can be seen that for purposes of the process defined and claimed herein six separate and distinct entitles are introduced into a reaction zone prior to subjecting them to an elevated temperature and elevated pressure sufficient to obtain ethanol. Of these the cobalt tricarbonyl complex, iodine and ruthenium entitles require further elucidation.

The cobalt tricarbonyl complex can be defined in accordance with the following formula:

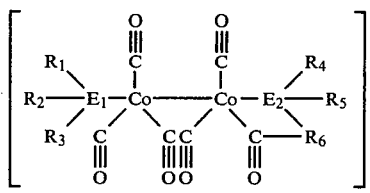

wherein $E_1$ and $E_2$ are either alike or different members selected from the group consisting of trivalent phosphorus, trivalent arsenic and trivalent antimony or mixtures thereof; wherein $R_1$, $R_2$, $R_3$, $R_4$, $R_5$ and $R_6$ are either alike or different members selected from the group consisting of saturated or unsaturated, straight or branched chain alkyl radicals having from one to 24 carbon atoms, preferably from one to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from about three to 40 carbon atoms, preferably from three to 30 carbon atoms; and aralkyl and alkaryl radicals having from six to 40 carbon atoms, preferably from six to 30 carbon atoms.

Cobalt tricarbonyl complexes which are suitable for use herein include:
triethyl phosphine cobalt tricarbonyl dimer
tri-n-butyl phosphine cobalt tricarbonyl dimer
tri-isopropyl phosphine cobalt tricarbonyl dimer
tricyclohexyl phosphine cobalt tricarbonyl dimer
tricycloheptyl phosphine cobalt tricarbonyl dimer
diphenyl-methyl phosphine cobalt tricarbonyl dimer
triphenyl phosphine cobalt tricarbonyl dimer
trinaphthyl phosphine cobalt tricarbonyl dimer
tristyryl phosphine cobalt tricarbonyl dimer
vinyl-diphenyl phosphine cobalt tricarbonyl dimer
tribenzyl phosphine cobalt tricarbonyl dimer
tri-para-tolyl phosphine cobalt tricarbonyl dimer
triethyl arsine cobalt tricarbonyl dimer
tri-n-butyl arsine cobalt tricarbonyl dimer
tri-isopropyl arsine cobalt tricarbonyl dimer
tricyclohexyl arsine cobalt tricarbonyl dimer
tricycloheptyl arsine cobalt tricarbonyl dimer
diphenyl-methyl arsine cobalt tricarbonyl dimer
triphenyl arsine cobalt tricarbonyl dimer
trinaphthyl arsine cobalt tricarbonyl dimer
tristyryl arsine cobalt tricarbonyl dimer
vinyl-diphenyl arsine cobalt tricarbonyl dimer
tribenzyl arsine cobalt tricarbonyl dimer
tri-para-tolyl arsine cobalt tricarbonyl dimer
triethyl antimony cobalt tricarbonyl dimer
tri-n-butyl antimony cobalt tricarbonyl dimer
tri-isopropyl antimony cobalt tricarbonyl dimer
tricyclohexyl antimony cobalt tricarbonyl dimer
tricycloheptyl antimony cobalt tricarbonyl dimer
diphenyl-methyl antimony cobalt tricarbonyl dimer
triphenyl antimony cobalt tricarbonyl dimer
trinaphthyl antimony cobalt tricarbonyl dimer
tristyryl antimony cobalt tricarbonyl dimer
vinyl-diphenyl antimony cobalt tricarbonyl dimer
tribenzyl antimony cobalt tricarbonyl dimer; and
tri-para-tolyl antimony cobalt tricarbonyl dimer,
or mixtures thereof.

Any source of iodine which is capable of disassociating, that is, ionizing to form free iodide ions, in the reaction medium, can be used as a promoter in the present invention. Illustrative examples of iodine compounds especially suitable for use herein include iodine, potassium iodide, calcium iodide, sodium iodide, lithium iodide, hydrogen iodide, methyl iodide, ethyl iodide, etc.

Any ruthenium compound can be used herein and can include, for example, ruthenium acetylacetonate, ruthenium trichloride, ruthenium tribromode, ruthenium dioxide, ruthenium triiodide, ruthenium acetate, ruthenium propionate, ruthenium octonate, ruthenium tetraoxide, ruthenium pentacarbonyl and tri-ruthenium dodecarbonyl.

The relative amounts of hydrogen and carbon monoxide employed can be varied over a wide range. However, in general, the molar ratio range of hydrogen to carbon monoxide is from about 10:1 to about 1:10, especially from about 3:1 to about 1:3; however, conventional synthesis gas (mixtures of hydrogen to carbon monoxide) with a ratio of about 1:1 is convenient and satisfactory for the process herein. It is to be noted that molar ratios outside the aforestated ratio ranges can be employed herein. Compounds or reaction mixtures which give rise to the formation of carbon monoxide and hydrogen under the reaction conditions defined herein can be used instead of mixtures comprising hydrogen and carbon monoxide, which are used in the preferred embodiments of this invention.

The cobalt, iodine and ruthenium entitles are introduced into the reaction zone in molar ratios, based on the elements cobalt, iodine and ruthenium, respectively, ranging from about 100:1:1 to about 1:10:2, preferably from about 20:1:1 to about 1:5:1. Based on the methanol introduced into the system, the weight percent of combined cobalt, iodine and ruthenium entitles, in their elemental form, can range from about 0.01 to about 10 percent, preferably about 0.1 to about five percent.

The process defined herein can be carried out either in a batch operation or by passing the reactants continuously through a reaction zone. In each case the reactor is provided with agitation means and the pressure is maintained therein by the addition of hydrogen and carbon monoxide as required. In order to facilitate introduction of the cobalt, iodine and ruthenium entitles into the reaction zone and/or to facilitate recovery of the components of the reaction herein, they can first be dissolved in an inert solvent, such as ethylene glycol, diethylene glycol, monomethyl ether, acetone, etc.

In the reaction zone the contents thereof are then maintained at an elevated temperature and an elevated pressure for a time sufficient to convert methanol to ethanol. Pressures which are suitable for use herein generally are above about 1000 pounds per square inch gauge (6.83 MPa), but should not be in excess of about 10,000 pounds per square inch gauge (68.30 MPa). An especially desirable pressure range is from about 1000 pounds per square inch gauge (6.83 MPa) to about 6000 pounds per square inch gauge (40.98 MPa), preferably from about 2000 pounds per square inch gauge (13.66 MPa) to about 5000 pounds per square inch gauge (34.15 MPa). Temperatures which are suitable for use herein are those temperatures which initiate a reaction between the reactants herein to produce ethanol, generally from about 150° C. to about 250° C., preferably from about 175° C. to about 225° C. The reaction is conducted for a time period sufficient to convert methanol to ethanol, normally from about 0.5 to about 10 hours, especially from about one to about five hours.

Recovery of the desired ethanol from the reaction product can be effected in any convenient or conventional manner, for example, by distillation. It should be noted that at ambient pressure (atmospheric pressure) and 21° C., the components will distill off, for example, in the following sequence for the desired recovery: dimethyl ether, acetaldehyde, methylacetate, methanol and ethanol.

The cobalt tricarbonyl complex, iodine promoter and ruthenium compound herein are highly selective to the formation of ethanol and minimize the formation of undesirable by-products such as acetaldehyde, ethers, esters and other alcohol derivatives. It should be noted that the cobalt tricarbonyl complex in combination with the iodine promoter and ruthenium compound is selective to producing at least 43.0 percent ethanol from the converted methanol.

DESCRIPTION OF PREFERRED EMBODIMENTS

The reactions herein are performed in a stainless steel pressure-resistant autoclave equipped with agitation means, for example, a 300 cc. type 316 stainless steel autoclave marketed commercially by Autoclave Engineers. The methanol, hydrogen, carbon monoxide, cobalt tricarbonyl complex, iodine promoter and ruthenium compound were introduced into the autoclave. The autoclave was connected to another larger reservoir containing synthesis gas (hydrogen and carbon monoxide) which fed said synthesis gas into the steel autoclave at a set pressure on demand. Thus, the reactor pressure was maintained throughout the course of the reaction. The reaction pressure and temperature were adjusted to operating conditions and the mixture reacted for a period of time sufficient to produce ethanol.

The following Examples and Tables serve to further illustrate and instruct one skilled in the art the best mode of how to practice this invention and are not intended to be construed as limiting thereof.

EXAMPLE I

Into a 300 cc. stainless steel autoclave were charged three millimoles of triphenyl phosphine cobalt tricarbonyl dimer, 1.5 millimoles of iodine, 0.75 millimole of ruthenium (III) acetylacetonate, and 100 milliliters of methanol. The reactor was next purged twice with nitrogen gas and then pressurized with synthesis gas (hydrogen to carbon monoxide molar ratio=1:1) to a pressure of about 1000 pounds per square inch gauge (6.83 MPa) lower than the desired working pressure, that is, 3000 pounds per square inch gauge (20.49 MPa). The system was then heated to a temperature of about 200° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter, a gas sample was taken for a mass spectral analysis, and the liquid product was analyzed using a Model 900 Perkins-Elmer gas chromatograph utilizing a 16 ft. (4.88 meters)×⅛ in. (0.32 centimeter) stainless steel column wherein 8 ft. (2.44 meters) of the column was packed with 80/100 mesh Poropak Q and other 8 ft. (2.44 meters) was packed with 80/100 Poropak R. Poropak Q and Poropak R are a form of poly-vinyl benzene marketed commercially by Waters Associates, a corporation located in Milford, Mass. The gas chromatograph was programmed to increase from 40° C. to 190° C. at a rate of 32° C./min. and with a helium flow rate of 30 cc./min.

An analysis indicated that 58.3 percent of the methanol was converted with the following mole percent selectivity:

| Compound | Selectivity, Mole Per Cent |
| --- | --- |
| Ethanol | 61.5 |
| Acetaldehyde | None |
| Dimethyl Ether | 3.5 |
| Diethyl Ether | 3.0 |
| Methyl Acetate | 13.4 |
| Other | 18.6 |

"Other" in this and other examples herein describes a mixture containing ethyl acetate, methyl formate, propanols, propionaldehyde, butanols, n-butyraldehyde and methane. From the above data, it is readily apparent that the triphenyl phosphine cobalt tricarbonyl dimer in combination with iodine and ruthenium acetylacetonate gives excellent selectivity in the conversion of methanol to ethanol in a single step. It is to be noted that any of the cobalt tricarbonyl complexes, the iodine promoters and ruthenium compounds herein can be substituted for the corresponding compounds above with substantially the same results.

EXAMPLE II

The procedure set forth in Example I was followed with the following exception: tri-n-butyl phosphine cobalt tricarbonyl dimer was substituted for the triphenyl phosphine cobalt tricarbonyl dimer. The reaction concentrations, temperature and pressure were as stated in Example I.

An analysis indicated that 43.9 percent of the methanol was converted with the following mole percent selectivity:

| Compound | Selectivity, Mole Per Cent |
| --- | --- |
| Ethanol | 72.1 |
| Acetaldehyde | None |
| Dimethyl Ether | 3.5 |
| Diethyl Ether | 3.0 |
| Methyl Acetate | 9.6 |
| Other | 11.8 |

Substitution of the other cobalt tricarbonyl complexes, iodine promoters or ruthenium compounds for the corresponding compounds above will produce substantially the same results.

EXAMPLE III

Methanol is selectively converted into ethanol by following the procedure of Example I with the following changes: tricyclohexyl phosphine cobalt tricarbonyl dimer, sodium iodide and ruthenium acetate are substituted for the corresponding compounds therein. The reaction will be highly selective to ethanol formation.

EXAMPLE IV

Ethanol is produced from methanol by reacting six millimoles of vinyl-diphenyl phosphine cobalt tricarbonyl dimer, 1.5 millimoles of potassium iodide, 0.75 millimole of tri-ruthenium dodecacarbonyl and synthesis gas ($H_2$:CO molar ratio=1:1) under the reaction conditions set forth in Example I. It is to be noted that the reaction will be highly selective to ethanol formation.

EXAMPLE V

Into a 300 cc. stainless steel autoclave were charged three millimoles of triphenyl arsine cobalt tricarbonyl dimer, 1.5 millimoles of iodine, 0.75 millimole of ruthenium (III) acetylacetonate, and 100 milliliters of methanol. The reactor was next purged twice with nitrogen gas and then pressurized with synthesis gas (hydrogen to carbon monoxide molar ratio=1:1) to a pressure of about 1000 pounds per square inch gauge (6.83 MPa) lower than the desired working pressure. The system was then heated to a temperature of about 200° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter, a gas sample was taken for a mass spectral analysis, and the liquid product was analyzed using a Model 900 Perkin-Elmer gas chromatograph utilizing a 16 ft. (4.88 meters)×⅛ in. (0.32 centimeter) stainless steel column wherein 8 ft. (2.44 meters) of the column was packed with 80/100 mesh Poropak Q and the other 8 ft. (2.44 meters) was packed with 80/100 Poropak R. The gas chromatograph was programmed to increase from 40° C. to 190° C. at a rate of 32° C./min. and with a helium flow rate at 30 cc./min.

An analysis indicated that 61.3 percent of the methanol was converted with the following mole percent selectivity:

| Compound | Selectivity, Mole Per Cent |
|---|---|
| Ethanol | 51.7 |
| Acetaldehyde | 13.0 |
| Dimethyl Ether | 3.9 |
| Diethyl Ether | 4.0 |
| Methyl Acetate | 12.4 |
| Other | 15.0 |

From the above data, it is readily apparent that the triphenyl arsine cobalt tricarbonyl dimer in combination with iodine and ruthenium acetylacetonate gives excellent selectivity in the conversion of methanol to ethanol in a single step. It is to be noted that any of the trivalent antimony and trivalent phosphorus cobalt tricarbonyl compounds herein can be substituted for the triphenyl arsine cobalt tricarbonyl above, any of the iodine promoters herein can be substituted for the iodine above, and any of the ruthenium compounds can be substituted for the ruthenium acetylacetonate above with substantially the same results.

EXAMPLE VI

The procedure of Example V is followed with the following exceptions: tri-para-tolyl arsine cobalt tricarbonyl dimer, calcium iodide, and ruthenium trichloride are substituted for the corresponding compounds. It is to be noted that the reaction which takes place will be highly selective to ethanol formation.

EXAMPLE VII

Methanol is converted into ethanol utilizing the procedure of Example V with the following substitutions: tri-isopropyl arsine, calcium iodide and ruthenium dioxide are used in place of the corresponding compounds in said Example. The reaction will produce ethanol in substantially high yields and will be very selective to the formation thereof.

EXAMPLE VIII

Into a 300 cc. stainless steel autoclave were charged three millimoles of triphenyl antimony cobalt tricarbonyl dimer, 1.5 millimoles of iodine, 0.75 millimole of ruthenium (III) acetylacetonate and 100 milliliters of methanol. The reactor was next purged twice with nitrogen gas and then pressurized with synthesis gas (hydrogen to carbon monoxide molar ratio=1:1) to a pressure of about 1000 pounds per square inch gauge (6.83 MPa) lower than the desired working pressure. The system was then heated to a temperature of about 200° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter, a gas sample was taken for a mass spectral analysis, and the liquid product was analyzed using a Model 900 Perkin-Elmer gas chromatograph utilizing a 16 ft. (4.88 meters)×⅛ in. (0.32 centimeter) stainless steel column wherein 8 ft. (2.44 meters) of the column was packed with 80/100 mesh Poropak Q and the other 8 ft. (2.44 meters) was packed with 80/100 Poropak R. The gas chromatograph was programmed to increase from 40° C. to 190° C. at a rate of 32° C./min. and with a helium flow rate at 30 cc./min.

The analysis indicated that 65.2 percent of the methanol was converted with the following mole percent selectivity:

| Compound | Selectivity, Mole Per Cent |
|---|---|
| Ethanol | 43.7 |
| Acetaldehyde | 17.7 |
| Dimethyl Ether | 3.9 |
| Diethyl Ether | 3.4 |
| Methyl Acetate | 14.8 |
| Other | 16.5 |

From the above data, it is readily apparent that the triphenyl antimony cobalt tricarbonyl dimer in combination with iodine and ruthenium acetylacetonate gives excellent selectivity in the conversion of methanol to ethanol in a single step.

EXAMPLE IX

Ethanol is produced from methanol using the procedure of Example VIII with the following exceptions: diphenyl-methyl antimony cobalt tricarbonyl dimer, hydrogen iodide and ruthenium triiodide are substituted for the corresponding compounds in said Example VIII. The reaction which takes place will be highly selective to ethanol formation.

EXAMPLE X

Methanol is selectively converted into ethanol by following the procedure of Example VIII with the following changes: trinaphthyl antimony cobalt tricarbonyl dimer, methyl iodide and ruthenium octonate are substituted for the corresponding compounds in said Example VIII with substantially the same results.

Obviously, many modifications and variations of the invention, as hereinabove set forth, can be made without departing from the spirit and scope thereof, and therefore only such limitations should be imposed as are indicated in the appended claims.

We claim:

1. A process for selectively producing ethanol which comprises introducing into a reaction zone (1) methanol, (2) hydrogen, (3) carbon monoxide, (4) a cobalt tricarbonyl complex defined by the following formula:

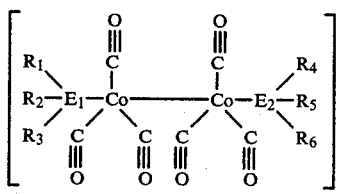

wherein each of $E_1$ and $E_2$ is trivalent phosphorus; and $R_1$, $R_2$, $R_3$, $R_4$, $R_5$ and $R_6$ are alike members selected from the group consisting of saturated or unsaturated, straight or branched chain alkyl radicals having from one to 24 carbon atoms; and aryl radicals having from six to 20 carbon atoms; (5) an iodine compound and (6) a ruthenium compound and then subjecting the contents of said reaction zone to an elevated temperature and an elevated pressure for a time sufficient to convert methanol to ethanol.

2. The process of claim 1 wherein $R_1$, $R_2$, $R_3$, $R_4$, $R_5$ and $R_6$ are selected from the group consisting of saturated or unsaturated, straight or branched chain alkyl radicals having from one to 10 carbon atoms; and aryl radicals having from six to 10 carbon atoms.

3. The process of claim 1 wherein the reaction time is about 0.5 hour to about 10 hours.

4. The process of claim 1 wherein the cobalt tricarbonyl complex is triphenyl phosphine cobalt tricarbonyl dimer.

5. The process of claim 1 wherein the cobalt tricarbonyl complex is tri-n-butyl phosphine tricarbonyl dimer.

6. The process of claim 1 wherein the reaction time is about one to about five hours.

7. The process of claim 1 wherein the molar ratios of hydrogen to carbon monoxide are about 10:1 to about 1:10.

8. The process of claim 1 wherein the molar ratios of hydrogen to carbon monoxide are about 3:1 to about 1:30.

9. The process of claim 1 wherein the iodine promoter is a member selected from the group consisting of iodine, potassium iodide, calcium iodide, sodium iodide, lithium iodide, hydrogen iodide, methyl iodide and ethyl iodide, or mixtures thereof.

10. The process of claim 1 wherein the iodine promoter is iodine.

11. The process of claim 1 wherein the ruthenium compound is a member selected from the group consisting of ruthenium acetylacetonate, ruthenium trichloride, ruthenium tribromide, ruthenium triiodide, ruthenium acetate, ruthenium propionate, ruthenium octonate, ruthenium dioxide, ruthenium tetraoxide, ruthenium pentacarbonyl and tri-ruthenium dodecacarbonyl, or mixtures thereof.

12. The process of claim 1 wherein the ruthenium compound is ruthenium acetylacetonate.

13. The process of claim 1 wherein the ruthenium compound is ruthenium acetate.

14. The process of claim 1 wherein the ruthenium compound is tri-ruthenium dodecarbonyl.

15. The process of claim 1 wherein the ruthenium compound is ruthenium dioxide.

16. The process of claim 1 wherein the ruthenium compound is ruthenium triiodide.

17. The process of claim 1 wherein the cobalt, iodine and ruthenium entitles are present in a molar ratio of about 100:1:1 to about 1:10:2.

18. The process of claim 1 wherein the cobalt, iodine and ruthenium entitles are present in a molar ratio of about 20:1:1 to about 1:5:1.

19. The process of claim 1 wherein the weight percent of the combined cobalt, iodine and ruthenium is in the range of about 0.01 to about 10 percent.

20. The process of claim 1 wherein the weight percent of the combined cobalt, iodine and ruthenium is in the range of about 0.01 to about five percent.

21. The process of claim 1 wherein the reaction temperature is about 150° C. to about 250° C.

22. The process of claim 1 wherein the reaction temperature is about 175° C. to about 225° C.

23. The process of claim 1 wherein the reaction pressure is about 1000 pounds per square inch gauge to about 10,000 pounds per square inch gauge.

24. The process of claim 1 wherein the reaction pressure is about 1000 pounds per square inch gauge to about 6000 pounds per square inch gauge.

25. The process of claim 1 wherein the reaction pressure is about 2000 pounds per square inch gauge to about 5000 pounds per square inch gauge.

* * * * *